United States Patent
Watts et al.

[11] Patent Number: 6,017,331
[45] Date of Patent: Jan. 25, 2000

[54] THREADED MEDICATION CARTRIDGE

[75] Inventors: Lennox Watts, Bronx, N.Y.; Roger W. Hoeck, Loomis, Nebr.; John Linfante, Brielle, N.J.; Daniel A. Walters, Rockaway Township, N.J.; Carlos A. Bustamante, Garfield, N.J.

[73] Assignee: Becton Dickinson and Company, Franklin Lakes, N.J.

[21] Appl. No.: 09/027,404

[22] Filed: Feb. 20, 1998

[51] Int. Cl.[7] ........................................ A61M 5/24
[52] U.S. Cl. ............................. 604/232; 604/201
[58] Field of Search ..................... 604/232–235, 604/181, 187, 134–138, 156, 157, 200, 201, 205

[56] References Cited

U.S. PATENT DOCUMENTS

| | | | |
|---|---|---|---|
| 2,870,766 | 1/1959 | Dann et al. | 604/232 |
| 3,459,177 | 8/1969 | Deuschle | 604/187 |
| 4,936,833 | 6/1990 | Sams | 604/232 |
| 5,405,326 | 4/1995 | Haber et al. | 604/110 |
| 5,554,134 | 9/1996 | Bonnichsen | 604/240 |
| 5,593,391 | 1/1997 | Stanners | 604/232 |
| 5,611,786 | 3/1997 | Kirchhofer et al. | 604/240 |

*Primary Examiner*—Wynn Wood Coggins
*Assistant Examiner*—Deborah Blyveis
*Attorney, Agent, or Firm*—Alan W. Fiedler

[57] ABSTRACT

A medication cartridge for use with a medication delivery pen having a cartridge body with threads at its distal end for receiving a pen-needle. The threads are either integrally molded in the cartridge or on the outer surface of a cap used to retain a septum on the distal end of the cartridge body. The cartridge body of the medication cartridge also includes threads or a snap-ring at its proximal end for attaching the medication cartridge directly to a pen body housing of the medication delivery pen without the need for a medication cartridge holder.

3 Claims, 7 Drawing Sheets

THREADED MEDICATION CARTRIDGE

BACKGROUND OF THE INVENTION

1. Field of the Invention

The present invention relates to a threaded medication cartridge for use with a medication delivery pen and, more specifically, a plastic or polypropylene medication cartridge having integral threads for receiving a threaded pen needle on its distal end and means for attaching the cartridge to a pen body housing at its proximal end.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula may be mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication may be drawn into the chamber of the syringe barrel by moving the plunger a selected distance in a proximal direction. The needle cannula may be withdrawn from the vial, and the medication may be injected into a patient by moving the plunger in a distal direction.

Some medication, such as insulin is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. One prior art medication delivery pen includes a vial holder into which a vial of insulin or other medication may be received. The vial holder is an elongate generally tubular structure with proximal and distal ends. The distal end of the prior art vial holder includes mounting means for engaging a double-ended needle cannula. The proximal end also includes mounting means for engaging a driver and dose setting apparatus as explained further below. A disposable vial for use with the prior art vial holder includes a distal end having a pierceable elastomeric seal that can be pierced by one end of a double-ended needle cannula. The proximal end of this prior art vial includes a plunger slidably disposed in fluid tight engagement with the cylindrical wall of the vial. This prior art medication delivery pen is used by inserting the vial of medication into the vial holder. A prior art pen body then is connected to the proximal end of the vial holder. The pen body includes a dose setting apparatus for designating a dose of medication to be delivered by the pen and a driving apparatus for urging the plunger of the vial distally for a distance corresponding to the selected dose.

The user of the pen mounts a prior art double-ended needle cannula to the distal end of the vial holder such that the proximal point of the needle cannula pierces the elastomeric seal on the vial. The patient then selects a dose and operates the pen to urge the plunger distally to deliver the selected dose. The dose selecting apparatus returns to zero upon injection of the selected dose with this prior art medication delivery pen. The patient then removes and discards the needle cannula, and keeps the prior art medication delivery pen in a convenient location for the next required medication administration. The medication in the vial will become exhausted after several such administrations of medication. The patient then separates the vial holder from the pen body. The empty vial may then be removed and discarded. A new vial can be inserted into the vial holder, and the vial holder and pen body can be reassembled and used as explained above.

The above described medication delivery pen is effective and much more convenient for self-administration of medication than the hypodermic syringes using separate medication vials. However, medication delivery pens like that described above have always required the use of a cartridge retainer to hold the medication cartridge therein with threads on the cartridge retainer or threads having to be attached to the cartridge itself to permit a conventional pen needle to be attached thereto. In addition, the disadvantage with current medication delivery pens is that the process of loading a cartridge into a pen requires numerous steps. The current cartridges also have a disadvantage in requiring a crimping operation be performed when the metal cap is attached to the distal end of the cartridge to hold the septum thereon.

Since it is particularly common among patients with diabetes to have complications of the disease causing impairment to fine motor skills, there is a strong need to address the problem of having so many steps required to load a vial into the medication delivery pen. Hence, it is necessary to provide a cartridge having integral threads for attaching a pen needle and integral means for attaching a cartridge to the pen body housing.

SUMMARY OF THE INVENTION

The present invention relates to a threaded cartridge for use with a medication delivery pen that addresses the above-identified problems by incorporating threads on the distal end of the cartridge for directly attaching a pen-needle and means on the proximal end of the cartridge for attaching the cartridge directly to a pen body housing of a medication delivery pen without the need for a cartridge retainer. For disposable pens this configuration also makes manufacturing easier, since one manufacturing step can be eliminated by eliminating the cartridge retainer used to hold the insulin cartridge.

DETAILED DESCRIPTION OF THE INVENTION

Figure 1:
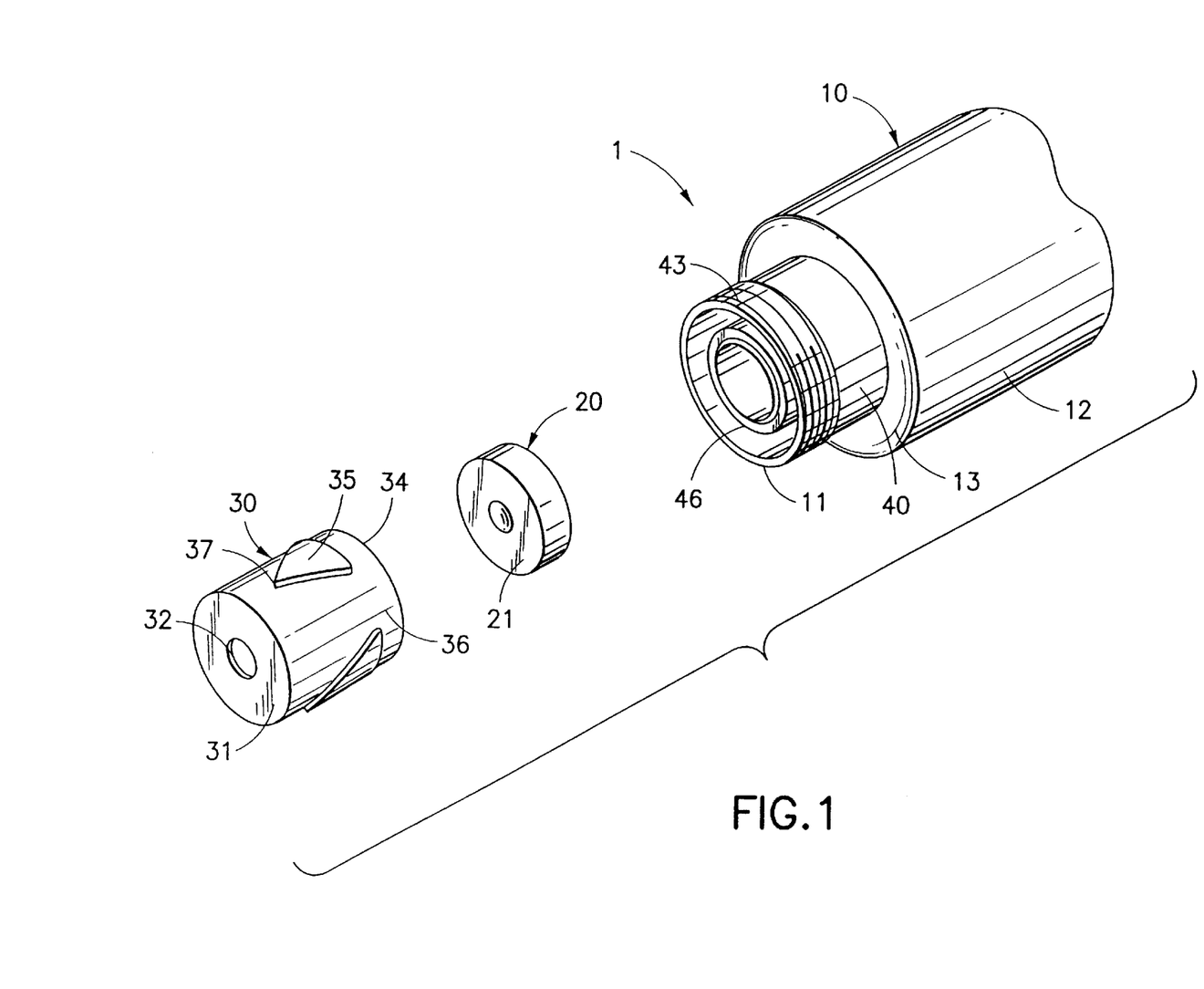
FIG. 1 is an exploded perspective view of the distal end of a medication cartridge according to the present invention.
Figure 2:
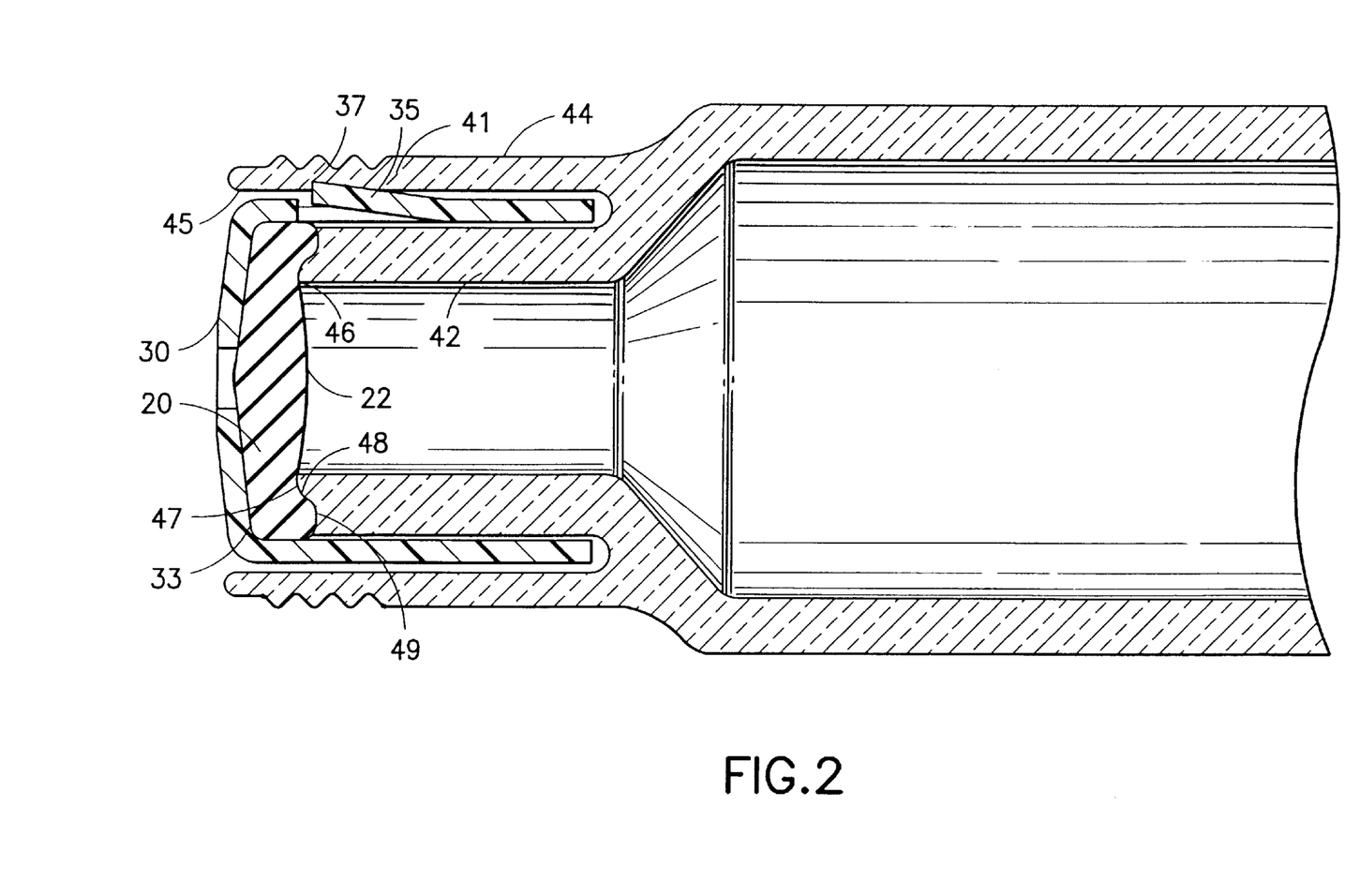
FIG. 2 is a cross-sectional view of the medication cartridge shown in FIG. 1 fully assembled.

FIG. 1 shows an exploded perspective view of a medication cartridge 1 including a cartridge body 10 made from polypropylene or other polymers and a septum 20 that is substantially flat with a distal face 21 and a proximal face 22, more clearly shown in FIG. 2. Septum 20 may also be laminated using a proximal bromobutyl layer and a distal layer made from isoprene material. Medication cartridge 1 also includes a septum retention cap 30 having a distal end 31 with an opening 32 and an inner surface 33, an open proximal end 34 and a plurality of triangular barbs 35 on an outer surface 36 with a point 37 of each barb 35 being directed in the distal direction.

Cartridge body 10 includes an open distal end 11 comprising a hub 40 extending from a shoulder 13 on a tubular container 12. Hub 40 includes an outer sleeve 41 having a thread 43 on an outer surface 44 for receiving a conventional pen needle and an inner surface 45. Hub 40 also includes an open inner sleeve 42 having a distal edge 46 that includes a raised ring 47 formed by an inner curved surface 48 leading to an outer tapered surface 49. In addition, outer sleeve 41 extends beyond distal edge 46 of inner sleeve 42.

As more clearly shown in FIG. 2, when cartridge 1 is fully assembled septum retention cap 30 is used to retain septum 20 on distal edge 46 of inner sleeve 42 on hub 40. Septum retention cap 30 is retained within hub 40 by points 37 on each triangular barb 35 being embedded into inner surface 45 of outer sleeve 41. It should be appreciated that no orientation is required for septum retention cap 30 when assembling septum 20 on to cartridge body 10. When fully assembled, opening 32 through distal end 31 of septum retention cap 30 provides access to septum 20 by the proximal point of a double ended conventional pen needle when the pen needle is removeably secured to hub 40. In addition, as shown in FIG. 2, inner surface 33 at distal end 31 of septum retention cap 30 is preferably parallel to outer tapered surface 49 on distal edge 46 of inner sleeve 42 within hub 40 to provide equal sealing forces across distal edge 46 and ensure a sufficient seal.

Figure 3:
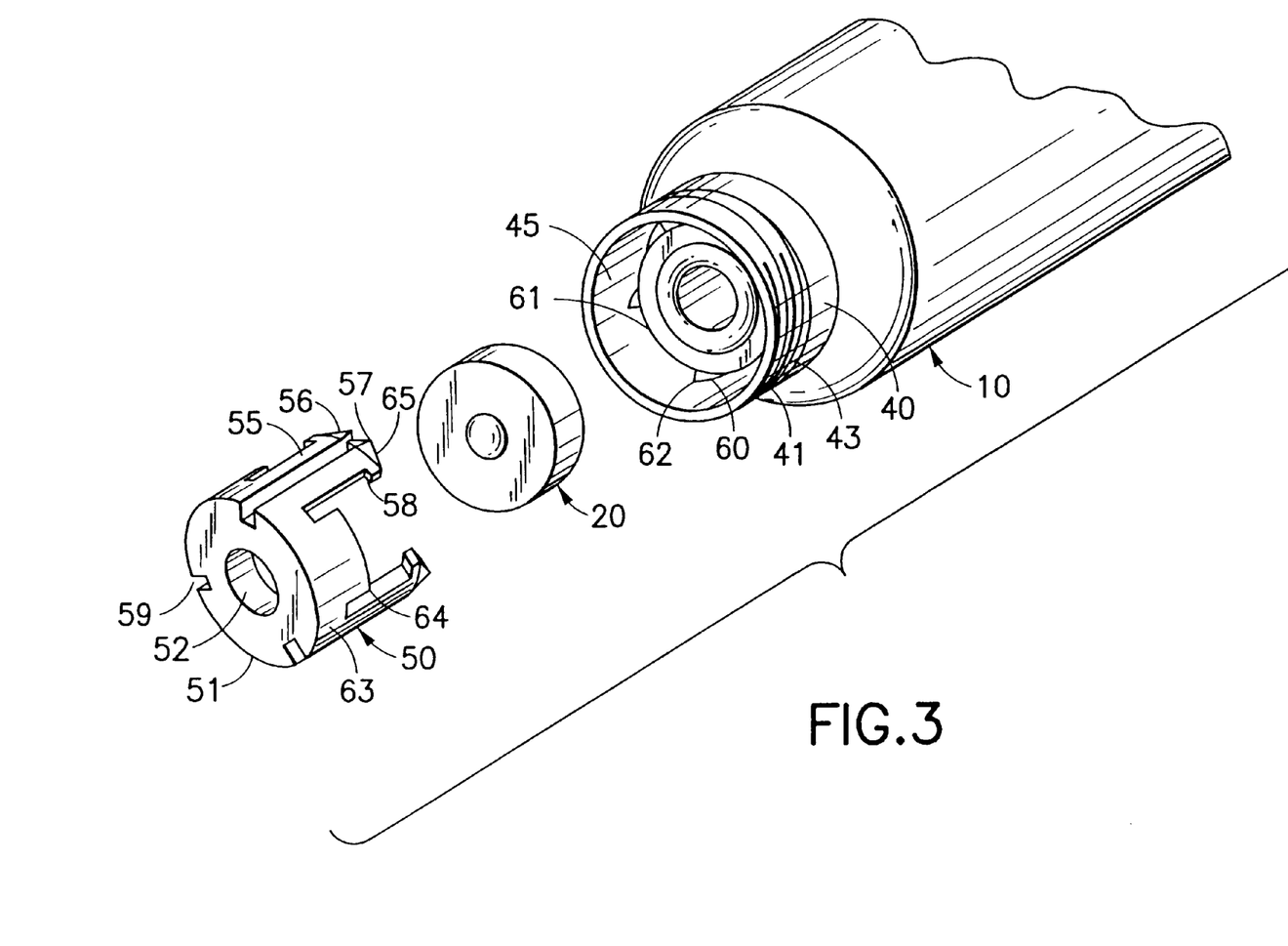
FIG. 3 is an exploded perspective view of an alternative medication cartridge according to the present invention.
Figure 4:
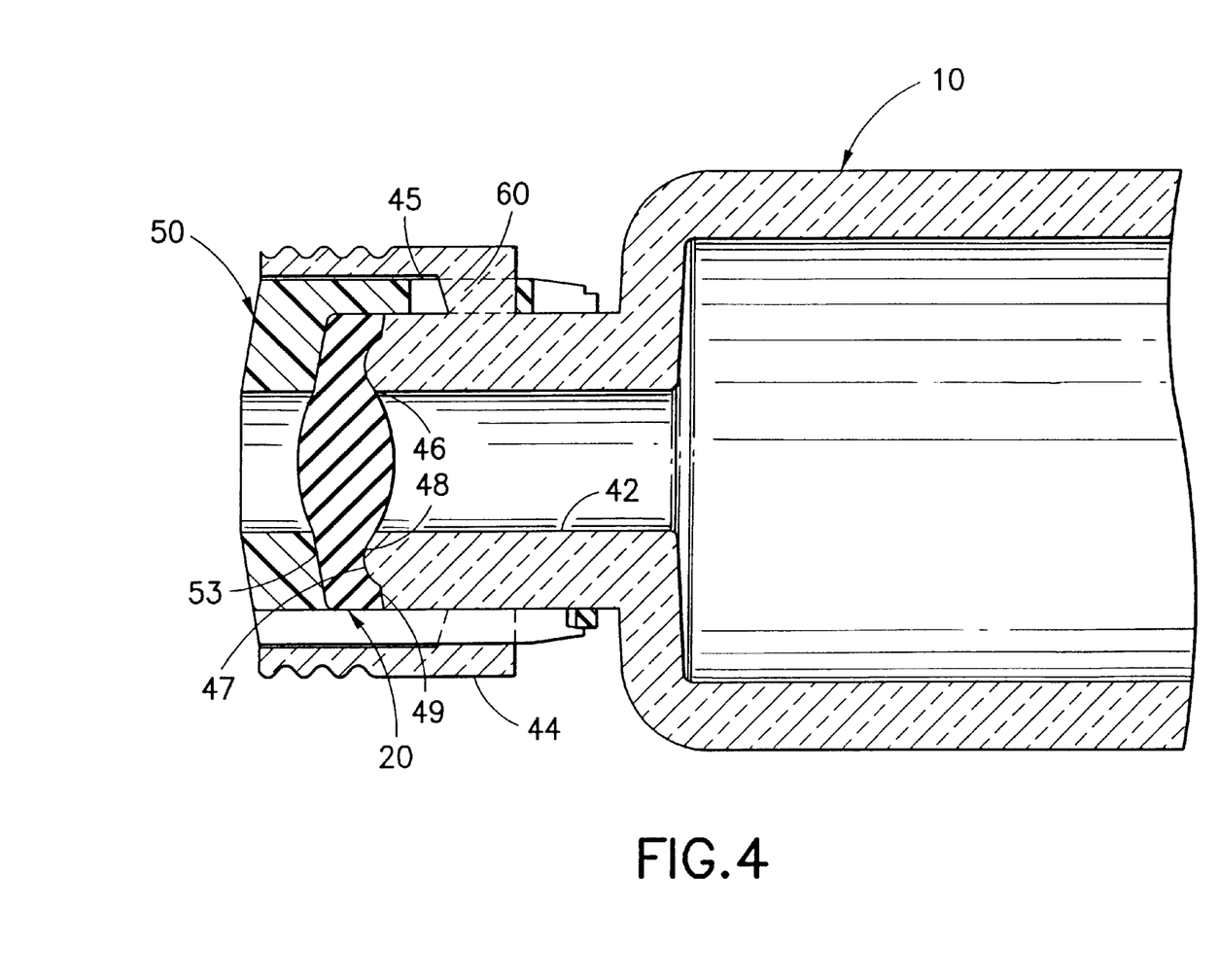
FIG. 4 is a cross-sectional view of the medication cartridge shown in FIG. 3 fully assembled.

FIGS. 3 and 4 show an alternative medication cartridge 10 having integral threads 43 formed on hub 40. This embodiment includes septum 20 having the same features as in the earlier embodiment, but has a different hub 40 and a different septum retention cap 50. Hub 40 includes an outer sleeve 41 with threads 43 on an outer surface 44 for receiving the threaded pen needle (not shown) and an inner surface 45. Hub 40 also includes an inner sleeve 42 having a distal edge 46 with a raised ring 47 formed by inner curved surface 48 leading to an outer tapered surface 49. However, outer sleeve 41 is attached directly to inner sleeve 42 by a plurality of connecting ribs 60 having spaces 61 therebetween. Ribs 60 are triangular in shape with a point 62 of each rib 60 extending in the distal direction so to guide each leg 55 into a respective space 61, as described below.

As shown in FIGS. 3 and 4, septum retention cap 50 includes a distal end 51 having an opening 52 and an inner surface 53, again preferably parallel to tapered surface 49 on inner sleeve 42, and a plurality of legs 55 extending in a proximal direction. Each leg 55 at its proximal end 56 includes an arrowhead 57 having shoulders 58. A flex slot 59 is formed in an outer surface 63 and extends from distal end 51 to proximal end 56 of arrowhead 57 and goes entirely through a portion of leg 55 to facilitate flexing of leg 55 during its assembly into hub 40. In addition, a pair of releaf slots 64 are positioned on either side of each leg 55 through outer surface 63.

The proximal side of each rib 60 in hub 40 is flat so to firmly secure shoulder 58 of arrowhead 57 at the end of each leg 55 when septum retention cap 50 is fully inserted and snapped into hub 40 to fully seal distal edge 46 on inner sleeve 42 in hub 40. As septum retention cap 50 is inserted into hub 40 proximal surfaces 65 on arrowhead 57 interact with triangular shape rib 60 to guide each leg 55 into a respective space 61 located between each pair of ribs 60 and thereby provide for snap engagement of both parts.

Figure 5:
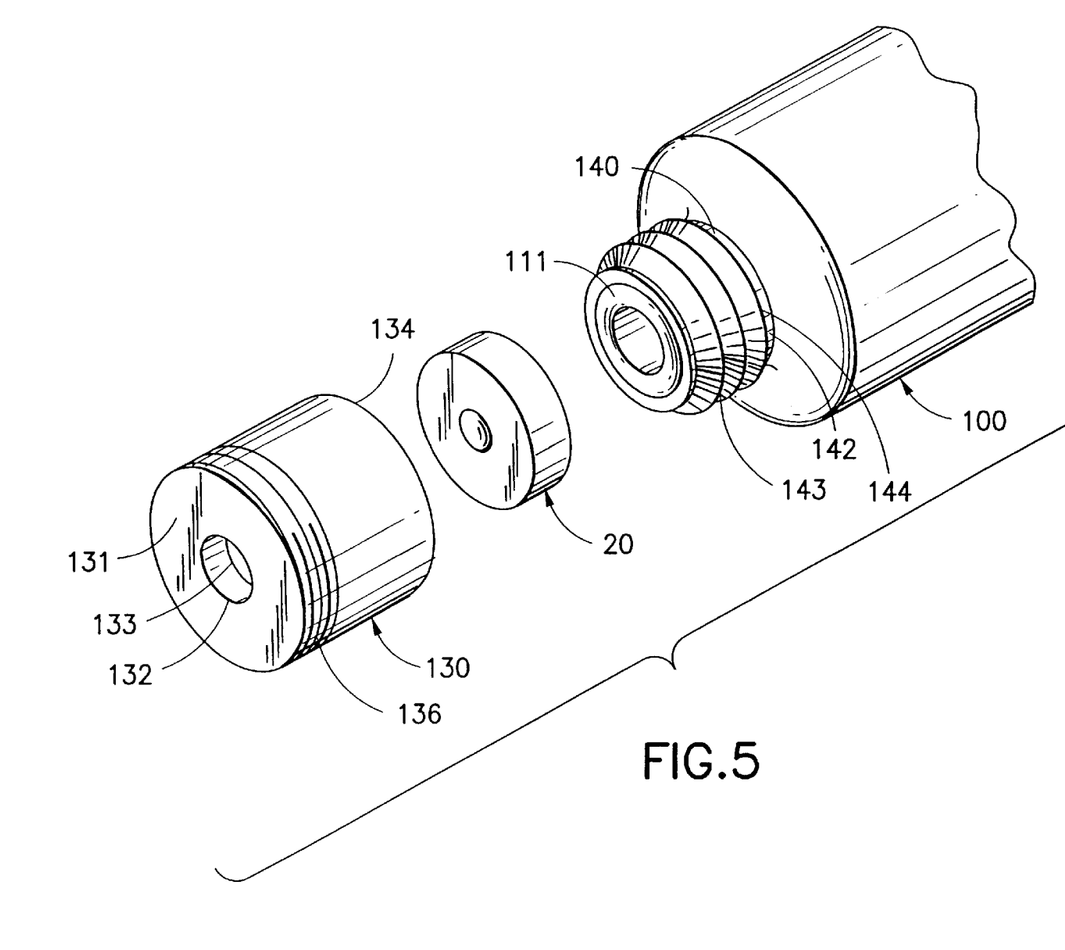
FIG. 5 is yet another medication cartridge according to the present invention.
Figure 6:
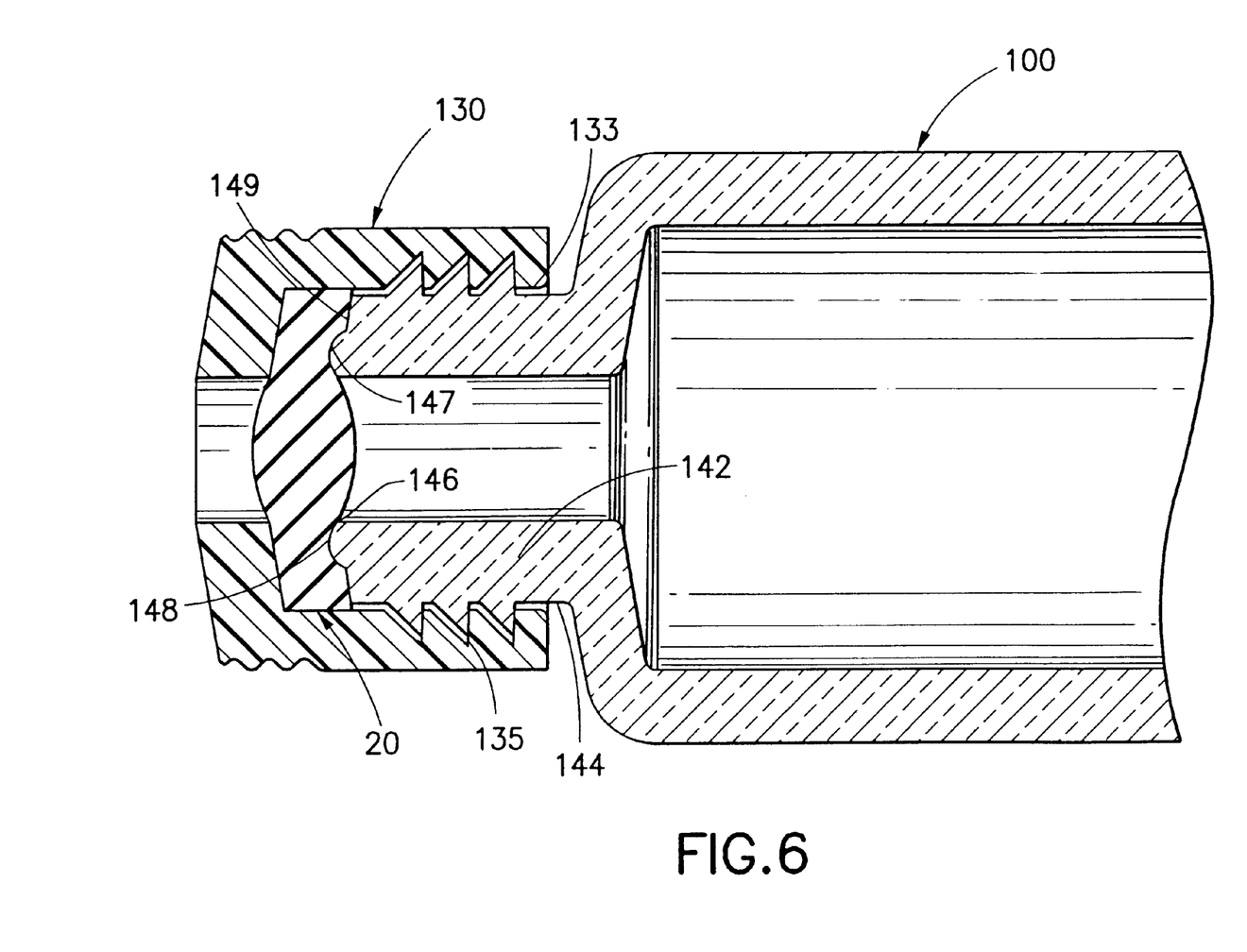
FIG. 6 is a cross-sectional view of the medication cartridge shown in FIG. 5 fully assembled.

FIGS. 5 and 6 show yet another embodiment of a cartridge according to the present invention. As shown in FIG. 5, cartridge body 100 includes a distal end 111 having a hub 140 comprised of a single sleeve 142 having one or more annular rings 143 protruding from an outer surface 144 of sleeve 142. As shown in FIG. 6, each annular ring 143 preferably has a triangular shape with a slope in the distal direction and a perpendicular surface in the proximal direction. Sleeve 142 includes a distal edge 146 having a raised ring 147 formed by an inner curved surface 148 leading to an outer tapered surface 149. Septum 20 is similar to septum 20 of the previous embodiments.

FIGS. 5 and 6 also show a septum retention cap 130 having a distal end 131 with an opening 132 and an inner surface 133 that again is preferably parallel to outer tapered surface 149 on sleeve 142. Septum retention cap 130 also includes a threaded outer surface 136 near distal end 131 and includes a plurality of triangular shaped recesses 135 on an inner surface 133 near open proximal end 134. The triangular shaped recesses 135 receive the annular rings 143 protruding from sleeve 142 to secure septum retention cap 130 on hub 140 and seal septum 20 therein.

Figure 7:
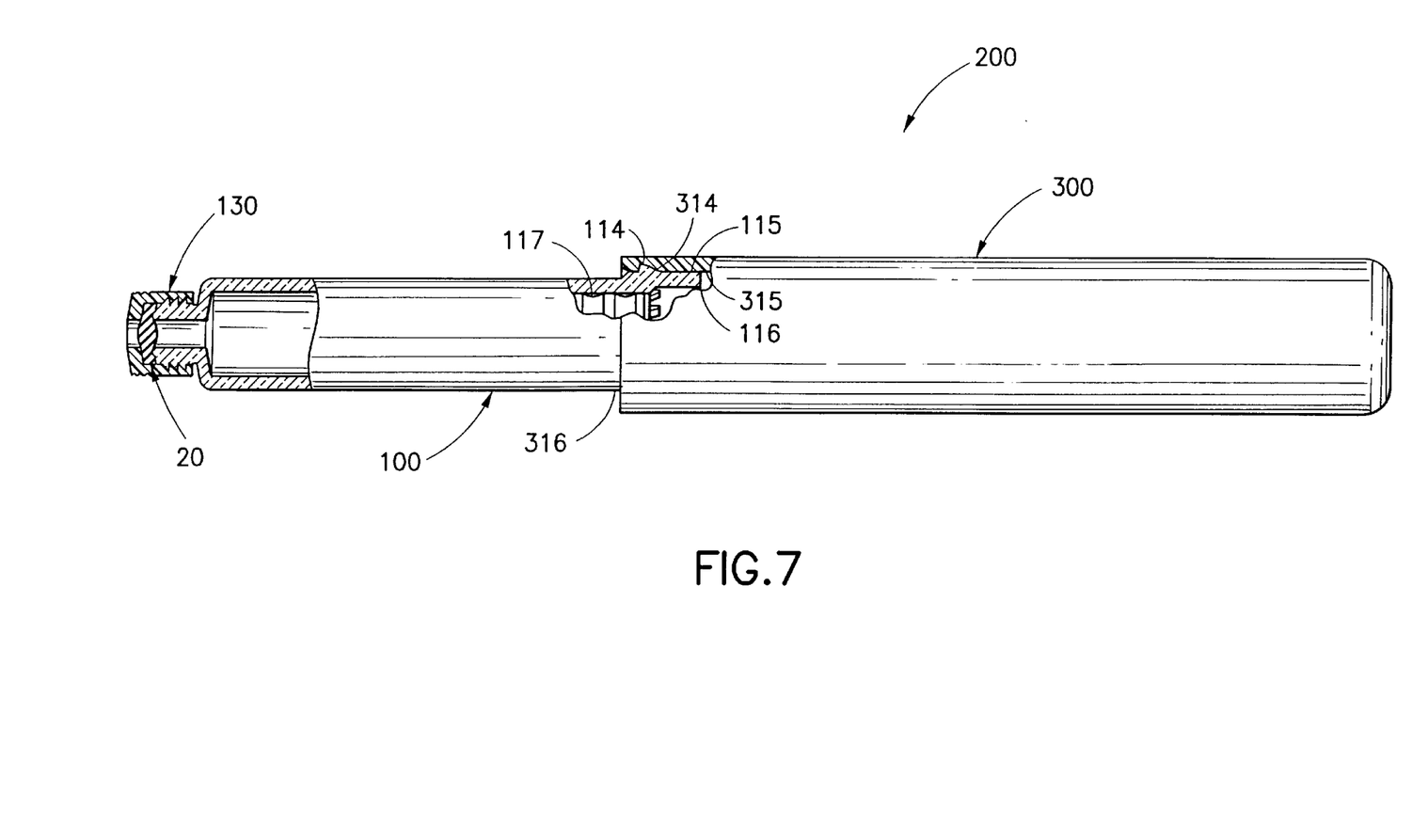
FIG. 7 is a plan view and a partial cross-sectional view of a medication delivery pen including the medication cartridge shown in FIGS. 5 and 6.

FIG. 7 is a plan view and partial cross-sectional view of a fully assembled medication delivery pen 200 including the medication cartridge shown in FIGS. 5 and 6. FIG. 7 shows means for attaching cartridge body 100 to a pen body housing 300 to provide a permanent snap-fit between these units. As shown in FIG. 7, means for attaching cartridge body 100 to pen body housing 300 includes a raised triangular ring 114 on outer surface 115 at a proximal end 116 of cartridge body 100 that is received by a triangular recess 314 on an inner wall 315 within pen body housing 300 near a distal end 316 of pen body housing 300. FIG. 7 also shows a plunger 117 within cartridge body 100 that is used to seal the open end of cartridge body 100 and to dispense medication from medication delivery pen 200.

Of course, the means shown for attaching cartridge body 100 to pen body housing 300 is merely exemplary since other means could be used to attach these parts and still fall within the scope of the present invention. In addition, while the present invention has been described with respect to a preferred and alternative embodiments, it is apparent that various other changes can be made without departing from the scope of the invention as defined by the appended claims.

What is claimed is:

1. A medication cartridge comprising:

a cartridge body having a distal end, a proximal end and a hub attached to said distal end, said hub including a set of threads and an outer sleeve attached to an inner sleeve by a plurality of connecting ribs having an opening between each rib;

a septum for mounting on said hub; and a septum retention cap for retaining said septum on said hub, said septum retention cap including a plurality of legs with each leg being received in one of said openings in said hub to retain said septum on said hub.

2. A medication cartridge according to claim 1, further comprising an arrowhead at a proximal end of each of said plurality of legs on said septum retention cap.

3. A medication cartridge according to claim 2, wherein each of said plurality of ribs has a triangular shape with a point in a distal direction to guide each arrowhead on said leg into a respective one of said plurality of openings.

* * * * *